United States Patent [19]

Davis

[11] Patent Number: 5,278,173

[45] Date of Patent: Jan. 11, 1994

[54] METHOD OF INHIBITING THE ACTIVITY OF HUMAN IMMUNODEFICIENCY VIRUS (HIV) IN VIVO

[76] Inventor: Michael H. Davis, 3020 E. Inglewood Ct., Springfield, Mo. 65804

[21] Appl. No.: 989,496

[22] Filed: Dec. 10, 1992

Related U.S. Application Data

[60] Continuation of Ser. No. 796,244, Nov. 25, 1991, abandoned, which is a division of Ser. No. 690,314, Apr. 25, 1991, Pat. No. 5,153,202, which is a continuation of Ser. No. 560,467, Jul. 27, 1990, abandoned, which is a continuation of Ser. No. 213,811, Jun. 30, 1988, abandoned.

[51] Int. Cl.$^5$ .................. A01N 43/42; A61K 31/47
[52] U.S. Cl. .................. 514/312; 514/885; 514/895
[58] Field of Search .................. 514/312, 885, 895

[56] References Cited

U.S. PATENT DOCUMENTS

| | | | |
|---|---|---|---|
| 4,835,140 | 5/1989 | Smith et al. | 514/24 |
| 4,970,212 | 11/1990 | Nowicky | 514/279 |
| 5,061,715 | 10/1991 | Sunkara et al. | 514/314 |

OTHER PUBLICATIONS

The Merck Index; Susan Budavari, ed; Merck & Co. Rahway, New Jersey, 1989, pp. 89 #602.

Kay et al., Southern Medical Journal, vol. 86, No. 4 pp. 403–404, Apr. 1990 "Clindamycin/Primaquine Therapy and Secondary Prophylaxis Against Pneumocystis carinii Pneumonia in Patients with AIDS".

Black et al, Eur. J. Clin. Microbiol. Infect. Dis., vol. 10, 1991 pp. 204–213, "Clindamycin and Primaquine as Primary Treatment for Mild . . . AIDS".

*Primary Examiner*—Nathan M. Nutter
*Attorney, Agent, or Firm*—Finnegan, Henderson, Farabow, Garrett & Dunner

[57] ABSTRACT

A method for inhibiting the activity of human immunodeficiency virus (HIV) in vivo comprises administering to a human host an antimalarial drug, which is capable of exhibiting a protective effect, a curative effect, or of preventing transmission of malaria in humans. The antimalarial drug is selected from the group consisting of (a) alkaloids;
(b) 9-amino-acridines;
(c) 4-aminoquinolines;
(d) 8-aminoquinolines;
(e) biguanides;
(f) dihyrofolate reductase inhibitors;
(g) sulfones;
(h) sulfonamides;
(i) mefloquine;
(j) halofantrine;
(k) hydroxyanilino-benzo-naphtyridines; and
(l) sesquiterpene lactones.

The antimalarial drug is administered to the human in an amount sufficient to prevent or at least inhibit infection of T lymphocytes by HIV in vivo or to prevent or at least inhibit replication of HIV in vivo.

7 Claims, No Drawings

METHOD OF INHIBITING THE ACTIVITY OF HUMAN IMMUNODEFICIENCY VIRUS (HIV) IN VIVO

This application is a continuation of U.S. Ser. No. 07/796,244, filed Nov. 25, 1991 and now abandoned, which is a divisional of application Ser. No. 690,314, filed Apr. 25, 1991 and now U.S. Pat. No. 5,153,202; which is a continuation application of Ser. No. 560,467, filed Jul. 27, 1990 and now abandoned; which is a continuation application of Ser. No. 213,811, filed Jun. 30, 1988 and now abandoned.

BACKGROUND OF THE INVENTION

This invention relates to the use of anti-malarial drugs for inhibiting infection of susceptible cells by human immunodeficiency virus (HIV). This invention also relates to a method of inhibiting proliferation of HIV.

Acquired immune deficiency syndrome (AIDS) is a condition which is now of major importance in North America, Europe, and Central Africa. The casual agent of AIDS is believed to be a retrovirus. Recent estimates suggest that approximately 1.5 million Americans may have been exposed to the AIDS virus. The individuals affected show severe immunosuppression, which may be followed by the onset of degenerative and even fatal diseases.

The isolation and characterization of the first AIDS retrovirus, known as LAV, was described in a paper by F. Barre-Sinoussi, et al. Science, 220:868-871 (1983). The use of some extracts of this virus and some of its proteins to detect antibodies against the virus is described in U.S. Pat. No. 4,708,818 issued to Dr. Luc Montagnier, et al.

Several isolates of the AIDS retrovirus were subsequently reported by different investigators and the isolates were referred to in the literature by different designations. It is now universally recognized that viruses previously denominated lymphadenopathy associated virus (LAV), immune deficiency associated virus (IDAV1 and IDAV2), human T-lymphotropic virus type III (HTLV-III), and AIDS related virus (ARV) are all variants of the same retrovirus. See, e.g., Nature, 313:636-637 (1985).

A subcommittee empowered by the International Committee on the Taxonomy of Viruses recently proposed that the AIDS retroviruses be officially designated as the "Human Immunonodeficiency Viruses", to be known in abbreviated form as "HIV". Isolates of human retroviruses with clear but limited relationship to isolates of HIV (for example, more than 20% but less than 50% nucleic acid sequence identity) are not to be called HIV unless there are compelling biological and structural similiarities to existing members of the group. Science, 232:697 (1986).

Another pathogenic human retrovirus, termed HIV-2 (formerly LAV-2), was recently recovered from West African patients with AIDS. Clavel et al., Science, 233:343-346 (1986). HIV-2 infection is associated with an immunodeficiency syndrome clinically indistinguishable from that caused by the prototype AIDS virus, HIV-1. HIV-2 is related to but distinct from HIV-1. Guyeder et al., Nature, 326:662-669 (1987).

Retroviruses genetically related and biologically similar to HIV have been isolated from subhuman primates. These retroviruses are designated as immunodeficiency viruses of the appropriate host species, such as, simian immunodeficiency virus (SIV). SIV was first isolated from captive rhesus macaques (Macaca mulatto) at the New England Regional Primate Research Center (NERPRC). This was soon followed by a report of isolation of an SIV called STLV-III from African green monkeys. Extensive serologic cross-reactivity exists between HIV-2 and SIV.

Transmission of HIV frequently takes place through sexual contact, although people using narcotics intravenously also represent a high-risk group. A large number of individuals have also been infected with HIV after receiving contaminated blood or blood products.

It is becoming more evident that other factors are important in the transmission of HIV in view of the occurence of AIDS in areas endemic of malaria. One factor felt etiologic in AIDS is defective Fc-receptor function in the reticuloendothelial system. B. S. Bender, J. Infect. Dis., 152:409-412 (1985). Defective Fc-receptor function on red blood cells and subsequent clearance of these IgG coated red cells has been demonstrated in AIDS patients. In addition, retrovirus antibody reactivity to the AIDS virus has shown considerable cross-reactivity with antibody levels against Plasmodium falciparum. R. J. Biggar et al., Lancet, Sep. 7, 1985:520-523. While there remains some debate about the cross-reactivity, R. J. Biggar et al., New Engl. J. Med., 315:57-8 (1986), A. E. Greenburg et al., Lancet, Aug. 2, 1986:247-249, this discussion does not take into account the possibility of dual exposure and clearance of the infective agent of AIDS accompanied by development of antibodies to the AIDS virus. The antibody cross-rectivity between AIDS and malaria is further exhibited by the effectiveness of a rather specific antimalarial agent in opportunistic infections. Pyrimethamine-sulfadoxine in combination has been shown effective in the treatment of Pneumocystis carinii infections in patients with AIDS. R. D. Pearson et al., Ann. Int. Med., 106:714-718 (1987).

The existence of multiple human immunodeficiency viruses, such as HIV-1 and HIV-2, presents a complex epidemiologic picture. There is a common belief that an effective vaccine or pharmaceutical composition against HIV infection must be developed in order to stem the spread of these retroviruses. Work is progressing on the development of a vaccine, but an effective agent has not yet been found. Thus, there exists a need in the art for a method of inhibiting the activity of HIV in vivo.

SUMMARY OF THE INVENTION

This invention aids in fulfilling these needs in the art. More particularly, this invention provides a method for inhibiting the activity of human immunodeficiency virus (HIV) in vivo, wherein the method comprises administering to a human host an antimalarial drug which is capable of exhibiting a protective effect, a curative effect, or of preventing transmission of malaria in humans. The antimalarial drug is selected from the group consisting of
 (a) alkaloids;
 (b) 9-amino-acridines;
 (c) 4-aminoquinolines;
 (d) 8-aminoquinolines;
 (e) biguanides;
 (f) dihydrofolate reductase inhibitors;
 (g) sulfones;
 (h) sulfonamides;
 (i) mefloquine;

(j) halofantrine;

(k) hydroxyanilio-benzo-naphtyridines; and (l) sesquiterpene lactones;

The antimalarial drug is administered to the human in an amount sufficient to prevent or at least inhibit infection of T lymphocytes by HIV in vivo or to prevent or at least inhibit replication of HIV in vivo.

The evasiveness and diversity of HIV has made a definitive treatment difficult. Presented here is an agent and a method capable of preventing the spread or acquisition of HIV infection and of assisting in the treatment of such infection.

DETAILED DESCRIPTION OF PREFERRED EMBODIMENTS

The method of this invention is useful for the treatment of humans either infected with HIV or susceptible to HIV infection. The expression "HIV infection" includes all of the types of infections included in the classification system published by the Centers for Disease Control, Atlanta, Ga. These infections include acute HIV infection; asymptomatic conditions; persistent generalized lymphadenopathy; and other diseases, such as constitutional disease, neurological disease, secondary infections, secondary cancers, and other conditions attributed to HIV infection or immunosuppression.

The method of the invention is especially useful for inhibiting the activity of HIV-1 or HIV-2 in humans infected therewith. While this invention is described with reference to human isolates identified in the literature as LAV-I, HTLV-III, and LAV-II, it will be understood that this invention extends to the same or equivalent retroviruses. These retroviruses are believed to be the causative agents of AIDS and HIV disease.

For the purpose of this disclosure, a virus is considered to be the same as or equivalent to LAV/HTLV-III if it substantially fulfills the following criteria:

(a) The virus is tropic for T-lymphocytes, especially T-helper cells (CD4+);

(b) The virus is cytopathic for infected CD4+ cells;

(c) The virus encodes an RNA-dependent DNA polymerase (reverse transciptase) which is $Mg^{2+}$-dependent and can employ oligo$(dT)_{12-18}$ as a primer for reverse transcription from its 3' LTR;

(d) The virus is substantially cross-reactive immunologically with the proteins encoded by the gag and env regions of LAV/HTLV-III; and (e) The virus shares substantial nucleotide homology (approximately 75-100%) and amino acid sequence homology (approximately 75-100%) with LAV or HTLV-III.

The principal pharmaceutically active ingredient employed in the method of the invention is an antimalarial drug. As used herein, the term "antimalarial drug" includes drugs that have a protective (prophylactic) effect against malarial infection, a curative (therapeutic) effect against malarial infection, or prevent transmission of malaria in humans. Thus, antimalarial drugs include drugs that are used before malaria infection occurs or before malaria infection becomes evident with the aim of preventing either the occurence of the infection or any of its symptoms. Antimalarial drugs also include drugs that are therapeutically used for their action on established malaria infection. Further, antimalarial drugs include drugs that are useful for the prevention of infection of humans by malarial vectors, including drugs that intervene or interfere with the malaria parasite life cycle in a human host.

Antimalarial drugs that can be employed in practicing the method of this invention are selected from the group consisting of the alkaloids, such as quinine and quinidine; 9-amino-acridines, such as mepacrine; 4-aminoquinolines, such as chloroquine and amodiaquin; and the 8-aminoquinolines, such as primaquine, pamaquine, and quinocide. Biguanides, such as proguanil (chlorguanide) can also be employed. Examples of other suitable antimalarial drugs are diaminopyrimidines, such as pyrimethamine, or other dihydrofolate reductase inhibitors, such as trimethoprim; sulfones, such as diaminodiphenyl sulfone (DDS or dapsone) and diformyl diphenyl sulfone; and sulfonamides, such as sulfadiazine, sulfamethoxypyrazine, sulfamonomethoxine, sulfadoxine, and sulfamethoxazole. Mefloquine; halofantrine; hydroxyanilino-benzo-naphtyridines, such as pyronaridine; and sesquiterpene lactones, such as artemisinine, can also be employed. These antimalarial drugs and methods of preparing the drugs are known in the art.

Combinations of one or more of the antimalarial drugs, other than pyrimethamine-sulfadoxine, can be employed in practicing the method of this invention. Thus, for example, pyrimethamine and chlorquine can be employed in combination. Similarly, amodiaquine can be employed together with primaquine, primethamine can be combined with dapsone, chloroquine can be employed with primaguanine or chlorproguanil, pyrimethamine or other antifolate drugs can be combined with sulfadoxine, and pyrimethamine can be employed together with sulfalene or sulfadiazine or sulfamethoxypyrazine.

The antibiotics used as antimalarial drugs have not been found to be effective when used alone-in the method of the invention. Thus, the expression "antimalarial drug" as used herein is intended to exclude antimalarial antibiotics when used alone in practicing the method of the invention. Nevertheless, it will be understood that antimalarial antibiotics, such as tetracycline and clindamycin (doxycycline, lincomycin), can be employed in combination with one or more of the aforementioned antimalarial drugs.

It will also be understood that the method of this invention can be practiced with compounds that change in vivo into one of the aforementioned antimalarial drugs, as well as compounds that produce metabolites in vivo similar to the metabolites formed from the aforementioned antimalarial drugs.

The antimalarial drugs can be employed in the form of the free base or in the form of a pharmaceutically acceptable acid addition salt. Examples of suitable salts are the chlorides, hydrochlorides, sulfates, phosphates, and diphosphates. Other water soluble, non-toxic, inorganic and organic salts can also be employed.

In practicing the method of the invention, the antimalarial drug is administered to a human host using one of the modes of administration commonly employed for administering the drug as an antimalarial agent to humans. Thus, for example, the drug can be administered to the host by the oral route or parenterally, such as by intravenous or intramuscular injection. For purposes of injection the compounds described above can be prepared in the form of solutions, suspensions, or emulsions in vehicles conventionally employed for this purpose. Other modes of administration can also be employed.

The antimalarial drug is employed in the method of the invention in an amount sufficient to provide an adequate concentration of the drug to prevent or at least inhibit infection of T lymphocytes by HIV in vivo or to prevent or at least inhibit replication of HIV in vivo. The amount of the drug thus depends upon absorption, distribution, and clearance by the human host. Of course, the effectiveness of the antimalarial drugs is dose related. The dosage of the antimalarial drug should be sufficient to produce a minimal detectable effect, but the dosage should be less than the established lethal dose. The dosage of the antimalarial drug administered to the host can be varied over wide limits. The compounds can be administered in the minimum quantity which is therapeutically effective and the dosage can be increased as desired up the maximum dosage tolerated by the patient. The antimalarial drug can be administered as a relatively high loading dose, followed by lower maintenance dose, or the drug can be administered in uniform dosages.

The dosage and the frequency of administration will vary with the antimalarial drug employed in the method of the invention. The antimalarial drugs can be employed in this invention in an amount of up to about 6 times the recommended maximum dosage for the treatment of malaria. Generally, the dosage will not exceed about 5 times the recommended maximum dosage for the treatment of malaria, and most often not more than about 4 times such recommended maximum dosage. Following are examples of suitable dosage levels.

Quinine dihydrochloride or sulfate can be orally administered in tablets containing 300-650 mg of the drug, 2-3 tablets daily. Liquid formulations of this drug can be administered by injection using solutions containing 300-500 mg/ml of the drug over a period of about 3-4 hours until 600 mg are administered, and the procedure can be repeated 2-3 times in 24 hours.

The antimalarial drugs chloroquine phosphate and chloroquine sulfate can be orally administered in tablet form (100 mg, 150 mg, and 300 mg) at 300 mg-600 mg over one week. Solutions of these antimalarial drugs can be intramuscularly or intravenously injected as 5% solutions at a dosage of 200-300 mg intramuscularly repeated in six hours or intravenously (drip) 300-600 mg in 500 ml saline.

Amodiaquaine hydrochloride or free base can be orally administered in tablets containing 200 mg of the drug at a rate of 400-2,000 mg over one week. As another example, primaquine diphosphate can be orally administered in tablets containing 5 mg-7.5 mg of the drug at a rate of 2-3 tablets per day.

Proguanil can be orally administered in tablets of 100 mg each at a rate of 1-2 tablets daily. Chlorproguanil can be orally administered in tablets containing 20 mg of the drug at a rate of 1 tablet per week. Similarly, tablets containing pyrimethamine (25 mg) can be administered at a rate of 1 tablet per week.

Mefloquine is also suitable for oral administration. Tablets containing 250 mg of the drug can be administered as a single or divided dose of 1,500 mg.

The dose of the antimalarial drug is specified in relation to an adult of average size. Thus, it will be understood that the dosage can he adjusted by 20-25% for patients with a lighter or heavier build. Similarly, the dosage for a child can be adjusted using well known dosage calculation formulas.

Primaquine through its more effective extraerythrocytic effect on the reticuloendothelial system and shedding of the virus is a preferred antimalarial drug for use in the method of the invention. The dose for adults is about 15 mg/day base (26 mg/day salt) orally or about 45 mg/wk base (79 mg/wk salt) orally. For children the dose is about 0.3 mg/kg per day base (0.5 mg/kg per day salt) orally or about 0.9 mg/kg per week base (1.5 mg/kg per week salt) orally.

As previously described, any of the antimalarial drugs can be employed in this invention at dosage levels that are multiples of the recommended dosage for the treatment of malaria. Thus, for example, the adult dose of primaquine can be up to about 250 mg/wk base. As another example, chloroquine can be employed in this invention at adult dosage levels of about 1800 mg/wk.

Because of the risk of hemolysis, particularly in individuals with glucose-6-P-dehydrogenase deficiency, other alternatives exist. These include the less toxic 8-aminoquinolines, or other carrier linked primaquine agents. J. Hofsteenge et al., J. Med. Chem., 29:1765-1769 (1986).

There is much speculation as to mechanism of action of the antimalarial drugs in the prevention and treatment of malaria. D. A. A. Akintonwa, J. Theor. Biol., 106:78-87 (1984). R. Deslauriers et al., Biochimica et Biophysica Acta, 931:267-275 (1987). Proposed mechanisms included inhibition of lysosomal cathepsins, protonation within acidic intracellular compartments, stabilization of membranes, and enzyme induction. The net effect of antimalarial drugs in the prevention and treatment of malaria appears to be in the inhibition of sporozoite invasion of reticuloendothelial cells. A. L. Schwartz et al., Molec. and Biochem. Parasit. 14:305-311 (1985). In any event, the mechanism by which the antimalarial drugs inhibit the activity of HIV in vivo by the method of this invention is not entirely understood. In fact, the mechanism may be due to one factor or to a combination of factors, such as a modification of one or more genotypic or phenotypic traits of the retrovirus or modification of viral or cellular processes. Thus, the antimalarial drug may inhibit infection of susceptible CD4+ cells by interfering with cell receptor function or the viral envelope receptor or by altering the nature of the binding mechanism. There is evidence that the retrovirus is translocated into the cell. Thus, the antimalarial drug may alter the translocation process. Further, the genomic elements that control the expression of the products required for viral replication may be altered or their functioning may be affected by the antimalarial drugs. Thus, for example, the antimalarial drugs may function as reverse transcriptase inhibitors or alter the nature of the envelope glycoprotein of the retrovirus or inhibit tat gene expression or affect the level of expression of the env gene determinants on the cell surface. The antimalarial drugs may also function by mediating the functioning of the reticuloendothelial system, either before or after HIV infection has occurred. For example, the antimalarial drugs may enhance Fc-receptor expression or function in vivo in the mononuclear phagocyte system. This may result in a lowered susceptibility to opportunistic infections associated with AIDS. The antimalarial drugs may also inhibit proliferation of HIV in infected phagocytic cells. It will be understood that the antimalarial drugs may function in any of these ways or by combinations thereof or by other ways not currently recognized. In any event, the antimalarial drugs can be administered to the patient in sufficient amounts to achieve one or more of these effects.

The effectiveness of the antimalarial drugs in preventing or inhibiting infection of cells is demonstrated using standard in vitro assays. Thus, the inhibitory effect of the antimalarial drugs on HIV infection or replication can be demonstrated by cultivating the virus or virus-infected cells in the presence and in the absence of the antimalarial drug and then comparing the results.

One method involves cultivation of normal peripheral blood mononuclear cells or other cultured cells exposed to the virus. The test for infectivity can use either free virus or virus-infected cells that are co-cultivated with a sensitive indicator cell. The virus replicates in the recipient indicator cell. By comparing viral replication in the absense of the antimalarial drug with viral replication in the presence of the drug, the inhibiting effect of the drug on HIV can be demonstrated.

Viral replication can be determined by monitoring reverse transcriptase (RT) activity. Virus production can also be determined by electron microscopic evidence of virus particles and various viral proteins. Various detection protocols for viral proteins make use of standard antibodies prepared against the virus in many animal species. Immunofluorescence can detect viral proteins rapidly and sensitive hyperimmune sera can be prepared. Radioimmune and ELISA assays can also be used to measure presence of viral proteins by competition in a system where a radiolabeled or colorimetrically identifiable antigen-antibody system can be perturbed by the addition of reactive antigen.

Another approach for demonstrating the effectiveness of the antimalarial drugs involves detection of the virus by detecting unintegrated and integrated viral DNA as well as viral mRNA. Nature, 312:166-169 (1984). Southern and Northern blot hybridization techniques are useful in determination of the relative amounts of viral DNA and RNA of the virus-harboring cells and tissues. Science, 227:177-182 (1985). A probe can be constructed for integrated provirus using molecularly cloned labeled proviral DNA, and then one can determine in a DNA transfer experiment whether there is a proviral genome integrated in cellular DNA by hybridization. If only a few cells contain the provirus, in situ hybridization can be attempted.

More particularly, in a typical experiment, cells are exposed to cell-free virions at a multiplicity of viral particles per cell and cultured in the presence or absence of antimalarial drugs. High molecular weight DNA is extracted at various times and assayed for its content of viral DNA using a radiolabelled HIV probe. Nature, 312:166-169 (1984). In the absence of antimalarial drugs under the culture conditions, viral DNA is detected. In contrast, in DNA from cells that have been completely protected by antimalarial drugs, neither unintegrated nor integrated DNA is detected.

It is also possible to monitor viral replication by determining whether viral RNA is expressed in target T cells exposed to the virus and cultured with or without antimalarial drugs. In this experiment, cells are exposed to HIV, and RNA is extracted from the cells. Extracted RNA is then assayed for the content of viral mRNA by Northern blot hybridization using a radiolabelled HIV antisense RNA probe. Science, 227:177-182 (1985). In the absence of dideoxynucleosides, viral mRNA is detectable. When these cultures are maintained for extensive periods of time in the presence of antimalarial drugs, viral RNA expression in the cells is not detected, or if detected, is present in substantially reduced amount. This assay system makes it possible to assess the capacity of the antimalarial drugs to inhibit HIV nucleotide synthesis and mRNA expression in T cells exposed to the virus.

In addition, HIV-I-infected cell lines MT2 and MT4 are sensitiveto the cytopathic effect of the virus. Thus, these cells can be used in plaque-forming assays to demonstrate the inhibitory effect of the antimalarial drugs on HIV infection or prolifertion. Science, 229:563-566 (1985).

The effectiveness of the antimalarial drugs in inhibiting HIV infection or HIV replication is also demonstrated in vitro by determining the inhibitory effect of the drugs on viral p24 gag protein expression in H9 cells, partially resistant to the cytopathic effect of HIV. M. Popovic et al, Science, 224:497-500 (1984). Following exposure of H9 cells to the virus, p24 antigen is determined by indirect immunofluorescence assay using murine monoclonal antibody. H9 cells are relatively resistant to the cytopathic effect of HIV, and p24 Sm protein expression following exposure to HIV can be used as an index of viral infectivity and replication in vitro. It is then possible to assess antiviral effect of the compounds by quantitating the HIV p24 gag protein expression in H9 cells that were exposed to the virus but cultured with drugs. Proc. Natl. Aca. Sci. USA, 82:4813-4817 (1985).

Anti-HIV activity can also be demonstrated by showing the inhibitory effect of the antimalarial drugs on the cytopathic effect of HIV. An immortalized helper-inducer T-cell clone (ATH8) has been described and shows the cytopathic effect of the virus. When ATH8 cells are cultured in a test tube, these cells form a pellet at the bottom of the tube and the pellet size reflects the number of viable target T cells. Under these conditions, the cytopathic effect is amenable to direct visual inspection. When exposed to HIV in the absence of the protective antimalarial drugs, the virus exerts a profound cytopathic effect on the target T cells. When the antimalarial drug is added in culture at the beginning of the assay, target ATH8 cells are protected against the cytopathic effect of the virus, and can continue to grow. These observations can be substantiated and quantitated by counting the number of viable cells with a dye exclusion method. This HIV cytopathic effect inhibition assay thus permits the simultaneous assessment of potential antiviral activity and toxicity of selective compounds. See, M. Hiroaki et al, Science, 240:646-649 (1988), for additional details of this assay.

Finally, the activity of the antimalarial drugs can be shown by normal T cells -in vitro. In this assay, normal cloned helper-inducer T cells, such as normal tetanus toxid-specific helper/inducer clonal T cells (TMII cells), are used to monitor the effect of the drugs on antigen-induced proliferative response. Details of this technique are described by H. Mitsuya et al., Science, 240:646-649 (1988).

The effectiveness of the antimalarial drugs in preventing or inhibiting HIV infection or replication can be confirmed in vivo with the chimpanzee. Persistent infection with HIV is demonstrated with this primate, although AIDS-like disease is not shown. The effectiveness of the antimalarial drugs can be demonstrated by comparing treated and untreated chimpanzees for seroconversion to HIV antigens, by reisolating infectious virus from the animals, by demonstrable lymphadenopathy, by alterations in T4 or TS lymphocyte levels, or by combinations of these factors.

HIV required to carry out these assays can be obtained from conventional sources using conventional techniques. For instance, mononuclear cells prepared from peripheral blood, bone marrow, and other tissues from patients and donors can be stimulated with mitogen (phytohemagglutinin-P) for 48 to 72 hrs and established in cell culture using growth medium supplemented with T cell growth factor (TCGF)., Virus can be detected by:

(1) monitoring supernatant fluids for viral reverse transcriptase activity; (2) transmitting virus to fresh normal human T-lymphocytes (e.g., umbilical cord blood, adult peripheral blood, or bone marrow leukocytes) or to established T-cell lines; M. Popovic et al, Science, 224:497 (1984); (3) electron microscopic observation of fixed and sectioned cells; and (4) testing for antigen expression by indirect immunofluorescence or Western blot procedures using serum from seropositive donors. The detection of virus-positive cells and the characterization and comparison of viral isolates can be conducted using HIV-specific immunologic reagents and nucleic acid probes. F. Barre-Sinoussi et al., Science, 220:868-871 (1983); R. C. Gallo et al., Science 220:865-867 (1983).

Many established cell lines have been tested as possible targets for HIV-1 infection. One neoplastic aneuploid T-cell line derived from an adult with lymphoid leukemia and termed HT is susceptible to infection with HTLV-III. HT cells continuously produce HTLV-III after parental cells are repeatedly exposed to concentrated cell culture fluids harvested from short-term cultured T-cells (grown in TCGF) that originated from patients with lymphadenopathy syndrome or AIDS. When cell proliferation declines, usually 10 to 20 days after exposure to the culture fluids, the fresh (uninfected) HT parental cells are added to cultures. To improve permissiveness for HIV and to preserve permanent growth and continuous production of virus, the HT cell population has been extensively cloned. Several of these clones of HT cells have been maintained in cell culture. In addition to HT, there are several other T or pre-T human cell lines that can be infected by and continue to produce HIV. Examples of these cell lines are H4, H9, HUT 78, CEM, Molt 3, and Ti7.4. Gallo et al., U.S. Pat. No. 4,652,599. Furthermore, some B-lymphoblastic cell lines can also be productively infected by HIV. L. Montagnier et al., Science, 225:63-66 (1984).

The antimalarial drugs and their pharmaceutically acceptable salts can be used in mammalian, including but not limited to human, therapy in the form of pills, tablets, lozenges, troches, capsules, suppositories, injectable or ingestable solutions and the like in the treatment of cytopatic and pathological conditions in humans and susceptible non-human primates caused by disturbances in the functioning of the immune systems, in particular as regards depression in the level of CD4+ T lymphocytes.

Appropriate pharmaceutically acceptable carriers, diluents, and adjuvants can be combined with the antimalarial compounds described herein in order to prepare the pharmaceutical compositions for use in the treatment of pathological conditions in mammals. The pharmaceutical compositions of this invention contain the active compound together with a solid or liquid pharmaceutically acceptable nontoxic carrier. Such pharmaceutical carriers can be sterile liquids, such as water and oils, including those of petroleum, animal, vegetable, or synthetic origin. Examples of suitable liquids are peanut oil, soybean oil, mineral oil, sesame oil and the like. Water is a preferred carrier when the pharmaceutical composition is administered intravenously. Physiological saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, magnesium carbonate, magnesium stearate, sodium stearate, glycerol monstearate, talc, sodium chloride, dried skim milk, glycerol, propylene glycol, water, ethanol, and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. The pharmaceutical compositions contain an effective therapeutic amount of the active compound together with a suitable amount of carrier so as to provide the form for proper administration to the host.

In summary, the antimalarial drugs are especially useful as antiviral agents for the therapeutic treatment of humans. They exhibit potent antiviral activity against the AIDS viruses, which is highly unusual and unexpected in view of the very limited and specific antiviral activity of the prior art antiviral agents. The antimalarial drugs exhibit marked suppression of HIV multiplication and virus-induced cell injury in animal and human cell tissue culture systems. The antimalarial drugs can reduce mortality and morbidity manifestations in humans, including a reduction in the occurrence of opportunistic infections associated with AIDS and a reduction in progressive, degenerative effects of HIV on the central nervous system.

What is claimed is:

1. A method for preventing or inhibiting the activity of human immunodeficiency virus (HIV) in vivo, wherein the method comprises administering a 4-aminoquinoline or a pharmaceutical salt thereof to a human in need thereof, in an amount sufficient to prevent or inhibit infection of T-lymphocytes by HIV or to prevent or inhibit replication of HIV in vivo.

2. The method of claim 1, wherein the 4-aminoquinoline is administered to the human in an admixture with a pharmaceutically acceptable carrier.

3. The method of claim 1, wherein the 4-aminoquinoline is selected from the group consisting of chloroquine, chloroquine phosphate, chloroquine sulphate, and amodiaquin.

4. The method of claim 1, wherein the 4-aminoquinoline is chloroquine.

5. The method of claim 1, wherein the 4-aminoquinoline is chloroquine phosphate.

6. The method of claim 1, wherein the 4-aminoquinoline is chloroquine sulphate.

7. The method of claim 1, wherein the 4-aminoquinoline is amodiaquin.

* * * * *